(12) United States Patent
La Nuez García et al.

(10) Patent No.: US 11,236,124 B2
(45) Date of Patent: Feb. 1, 2022

(54) METHOD AND COMPOSITION FOR HYDROLYZING EGGSHELL MEMBRANE

(71) Applicant: EGGNOVO S.L., Villatuerta (ES)

(72) Inventors: Manuel A. La Nuez García, Barañáin (ES); Andrés Aguirre González, Mutilva (ES)

(73) Assignee: EGGNOVO S.L., Villatuerta (ES)

( * ) Notice: Subject to any disclaimer, the term of this patent is extended or adjusted under 35 U.S.C. 154(b) by 197 days.

(21) Appl. No.: 16/629,549

(22) PCT Filed: Jul. 3, 2018

(86) PCT No.: PCT/ES2018/070473
§ 371 (c)(1),
(2) Date: Jan. 8, 2020

(87) PCT Pub. No.: WO2019/012170
PCT Pub. Date: Jan. 17, 2019

(65) Prior Publication Data
US 2020/0270302 A1    Aug. 27, 2020

(30) Foreign Application Priority Data
Jul. 12, 2017 (ES) ................ ES201730923

(51) Int. Cl.
*C07K 1/12* (2006.01)
*C12N 9/64* (2006.01)

(52) U.S. Cl.
CPC ............. *C07K 1/12* (2013.01); *C12N 9/641* (2013.01); *C12Y 304/22002* (2013.01)

(58) Field of Classification Search
CPC .......... C12N 9/641; C07K 1/12; C12P 21/06; A61P 17/00; A61P 19/02; C12Y 304/22002
See application file for complete search history.

(56) References Cited

U.S. PATENT DOCUMENTS

2010/0041606 A1*  2/2010  Elias .............................. 514/12

FOREIGN PATENT DOCUMENTS

| CN | 105821097 A | 8/2016 |
|---|---|---|
| EP | 2612922 A1 | 7/2013 |

* cited by examiner

*Primary Examiner* — Satyendra K Singh
(74) *Attorney, Agent, or Firm* — Wiggin and Dana LLP; Gregory S. Rosenblatt; Brian A. Pattengale

(57) ABSTRACT

The present invention relates to a method for hydrolyzing eggshell membrane, comprising the step of treating a suitable amount of eggshell in a solution containing a denaturing agent, a reducing agent, a buffer, and an enzyme. The invention also relates to a composition for hydrolyzing eggshell membrane according to the preceding method.

5 Claims, 1 Drawing Sheet

English Translation

METHOD AND COMPOSITION FOR HYDROLYZING EGGSHELL MEMBRANE

FIELD OF THE INVENTION

The present invention generally relates to the field of obtaining soluble protein products, and more specifically to hydrolyzing eggshell membrane.

BACKGROUND OF THE INVENTION

Eggshell membrane is very rich in metabolites of biological interest such as collagen, elastin, glycosaminoglycans (hyaluronic acid, chondroitin sulfate, heparan sulfate, dermatan sulfate), as well as glucosamine. It has been published in some studies that more than 500 proteins involved in the eggshell mineralization process as well as embryo protection have been identified in eggshell membrane, all of them being highly valuable constituents that may be used as a supplement aimed at improving skin and joint quality.

The generation of large amounts of eggshell by the industry therefore provides many opportunities for obtaining two fundamental raw materials: calcium carbonate (inorganic part of the shell) and membrana testacea consisting of two membranes, an inner membrane and another outer membrane, which are cross-linked by means of fibers forming a tight mesh rendering the structure thereof insoluble.

A technical problem relating to the insoluble nature of eggshell membrane is in fact known in the industry. Specifically, this insolubility is caused by the fibrous nature and the structural composition of the membrane; specifically, it is largely due to the cross-linking of collagen with elastin and keratin, in addition to the abundant disulfide bonds that are part of this framework.

In the field of protein solubilization in general, proteins must be broken down to the point where they can be integrated in the solution, something which is achieved by means of hydrolysis. Alkaline or acidic hydrolysis having the drawback of breaking down part of the composition of the original protein, reducing its nutritive value or even eliminating constituents such that precise protein characterization is not allowed, are generally applied. Another type of hydrolysis that is widely used for obtaining hydrolyzed proteins is the enzymatic pathway. Many protein by-products of the industry are put to good use through this process, as is the case of obtaining fish hydrolysates and whey, which are used as supplements in the food industry since they maintain their nutritional quality.

There are therefore three fundamental ways for solubilizing proteins: acidic hydrolysis, alkaline hydrolysis, and enzymatic hydrolysis. As mentioned above, both acidic and alkaline hydrolysis have the drawback of destroying some constituents of interest and reducing the nutritional value of some proteins. Enzymatic hydrolysis has the advantage of applying mild conditions which allow obtaining a product with better nutritional characteristics and possible bioactivities, and is therefore preferable. However, in the case of eggshell membrane a conventional enzymatic hydrolysis cannot be applied due to the membrane being highly enzyme-resistant.

Document EP 2612922 A1 discloses a method for solubilizing eggshell membrane by means of using a protease and a reducing agent; said method, however, does not provide acceptable efficiency. Therefore, it would be desirable to have a method for hydrolyzing eggshell membrane which provides improved solubilization yields.

When dealing with proteins that are extremely difficult to hydrolyze, the use of combinations of several proteinases (a cocktail) for an effective hydrolyzation is also known. Nevertheless, the use of a combination of enzymes increases method costs.

Therefore, it would also be desirable to have a method which allows obtaining suitable eggshell membrane solubilization efficacy with a single proteinase such that it allows performing precise analysis of the eggshell membrane constituents, maintaining a high integrity of the proteins and of the rest of the metabolites that are present with a minimum method cost.

SUMMARY OF THE INVENTION

To solve the problems of the prior art, the present invention discloses according to a first aspect a method for hydrolyzing eggshell membrane, comprising the step of treating a suitable amount of eggshell membrane in a solution containing a denaturing agent, a reducing agent, a buffer, and an enzyme.

According to a second aspect, the present invention also discloses a composition for hydrolyzing eggshell membrane suitable for use in the method of the first aspect of the present invention. Specifically, the hydrolyzation composition comprises a denaturing agent, a reducing agent, a buffer, and an enzyme.

BRIEF DESCRIPTION OF THE DRAWINGS

The present invention will be better understood in reference to the following drawings illustrating a preferred embodiment of the invention, provided by way of example, which must not be interpreted as limiting the invention in any way.

DETAILED DESCRIPTION OF THE PREFERRED EMBODIMENTS

Figure 1:
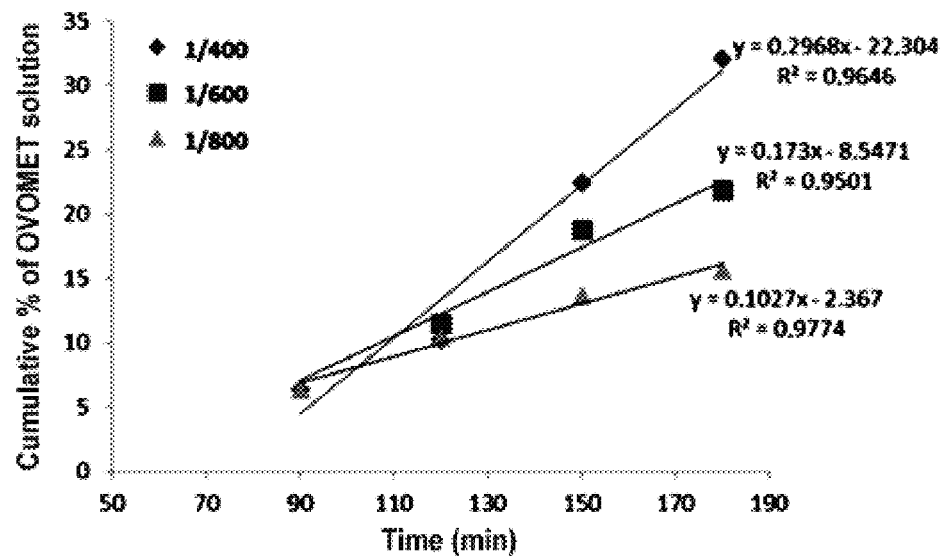
FIG. 1 is a graph showing the cumulative percentage of OVOMET solution as a function of time for different dilution ratios.

As mentioned above, the present invention discloses a method for hydrolyzing eggshell membrane as well as a composition for use in said method. Given that eggshell membrane is extremely resistant to degradation and solubilization explained above, the method according to the present invention resorts to the use of additives which can denature the proteins such that the enzymes can more readily access the bonds on which they perform their action.

Therefore, the method according to the preferred embodiment of the present invention comprises treating a suitable amount of eggshell membrane in a solution containing a denaturing agent, a reducing agent, a buffer, and an enzyme, such that the main biological components of the membrane in the resulting product can be quantified without any type of interference, and the membrane hydrolysates thus obtained can then be used as raw materials in the preparation of food supplements, dermocosmetic products, and biopharmaceutical products, among others.

The preferred embodiments of the present invention include one or more of the following characteristics:
  the denaturing agent has detergent properties and an amphiphilic nature, and is preferably an anionic surfactant, more specifically sodium lauryl sulfate (SDS) or sodium taurocholate;

the reducing agent has a sulfurated nature, can break disulfide bridges, will not generate interferences in subsequent quantifications, and is selected from the group consisting of food additives, more specifically sodium hydroxymethanesulfinate ($HOCH_2SO_2Na$), sodium metabisulfite ($Na_2S_2O_5$), and dithiothreitol (DTT), more preferably it is selected from sodium metabisulfite and DTT, and even more preferably it is sodium metabisulfite;

the enzyme is a protease of plant origin with endopeptidase activity from the group of cysteine proteases, preferably selected from the group consisting of papain and bromelain.

To achieve proper eggshell membrane hydrolyzation, the quaternary, tertiary, and secondary structures of the eggshell membrane must first be altered so that the enzymes can finally access said membrane and hydrolyze it. To that end, the purpose of using a denaturing agent is to break the two- and three-dimensional structure of the proteins through the addition of a negative charge to the amino acids. In this manner, as the proteins repel one another, their entanglement comes undone and access of the enzyme for hydrolysis becomes easier.

During the experiments, denaturing agents without detergent properties, such as urea, were tested without obtaining satisfactory dissolution results. However, when testing denaturing agents with detergent properties, such as SDS and taurocholate, excellent results were surprisingly obtained. Without wishing to be bound to any theory, it is believed that the structure of these detergents, which has a polar portion and another non-polar portion (amphiphilic nature), causes non-polar products to be integrated in the aqueous solution.

Due to the large number of disulfide bridges existing in the proteins of eggshell membrane, it was observed that in addition to using a denaturing agent it was necessary to use a reducing agent capable of breaking said disulfide bridges which caused some quaternary structures to remain unaltered after the use of the denaturing agent. To that end, several reducing agents were studied with surprising results being obtained for dithiothreitol (DTT) and sodium metabisulfite ($Na_2S_2O_5$).

Without wishing to be bound to any specific theory, the following scheme shows a possible mode of action of the additives used (denaturing agent and reducing agent) on the protein structure:

Scheme 1

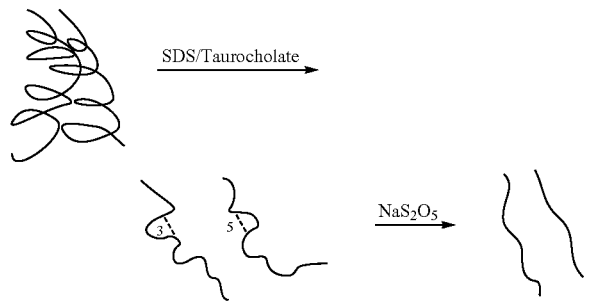

It is observed in the scheme that following the action of the SDS or taurocholate, the proteins are exposed to receive the attack of the enzyme. The reducing agent ends up leading the proteins to have a denatured structure. Once peptides are formed due to the action of the enzyme, the SDS or taurocholate maintains them in solution.

Once it was demonstrated that the enzymes, which are ultimately responsible for product hydrolysis, could fully access the proteins of the eggshell membrane, different enzymes were selected for efficiency testing. To that end, different endopeptidases were evaluated because the objective was to separate the peptide bonds from the center of the proteins. On the other hand, given the large amount of cysteine residues in eggshell membrane, in addition to the fact that disulfide bridges are established through the sulfur groups of said amino acid, it was suitable to select enzymes belonging to the family of cysteine proteases. The efficacy of different enzymes was tested, and it was observed that cysteine proteases were in fact the most suitable.

Therefore, the preferred embodiments of the present invention provide a method as well as a composition for suitably hydrolyzing eggshell membrane. Said method and composition for hydrolyzing eggshell membrane may have several uses in the art. For example, according to a preferred embodiment the method and the composition for hydrolyzing eggshell membrane allow determining the constituents of interest of the membrane (GAG, collagen, etc.) and using them as quality parameters to be taken into account for the purpose of comparing similar products on the market.

In a preferred embodiment, the method of the present invention comprises the step of treating an amount of eggshell membrane in a range of between 5 and 155 mg/ml, in another preferred embodiment in a range of between 20 and 150 mg/ml, and yet in another preferred embodiment in a range of 70 mg/ml, in a solution containing sodium metabisulfite in a range of between 50 and 150 mM, in another preferred embodiment in a range of 100 mM, 0.5-5% SDS in 25-50 mM HEPES buffer, in another preferred embodiment in a range of 50 mM, adjusted to a pH between 6 and 7, in another preferred embodiment in a range of 6.2, a 1% papain solution in sodium chloride in a range of 0.05 to 0.5 M, in another preferred embodiment in a range of 0.15 M, being added to said solution until the final papain concentration in the solution is 0.05-0.5%.

According to another preferred embodiment of the invention, the method and the composition for hydrolyzing eggshell membrane allow obtaining a soluble eggshell membrane product for the purpose of being obtained on an industrial scale and being used in various consumption sectors, for example in the sector of food supplements, cosmetics, biopharmaceutical products, etc.

In another preferred embodiment, the composition of the present invention comprises sodium metabisulfite in a range of between 50 and 150 mM, in another preferred embodiment in a range of 100 mM, 0.5-5% SDS in 25-50 mM HEPES buffer, in another preferred embodiment in a range of 50 mM, adjusted to a pH between 6 and 7, in another preferred embodiment in a range of 6.2, and 0.05-0.5% papain.

Several preferred embodiments of the present invention will be described in greater detail below by means of specific examples, without the invention being limited to said examples in any way.

Example 1

Assessment of Different Reducing Agents

A solution for solubilizing eggshell membrane was prepared at a ratio of 10 mg of eggshell membrane/ml of solution. Said solution comprised a denaturing agent, and more specifically a denaturing agent having detergent properties and an amphiphilic nature such as SDS, at a concentration of 0.5-5%. The solution also comprised a reducing agent, for which solutions of the following reducing agents were prepared at a concentration of 100 mM-1 M: sodium sulfite ($Na_2SO_3$), sodium hydrosulfite ($Na_2S_2O_4$), sodium hydroxymethanesulfinate ($HOCH_2SO_2Na$), sodium metabisulfite ($Na_2S_2O_5$), and dithiothreitol (DTT); these solutions were tested successively. Finally, a suitable buffer was added for maintaining the pH depending on the enzyme that was going to be used, having a concentration of 25-50 mM. Once the pH was adjusted with a pH-meter to the optimum pH for each enzyme, the enzyme previously prepared according to the manufacturer's specification at a concentration of 1% was added to the solution, such that the final concentration of the enzyme with respect to the total solution was 0.05-0.5%. The same was performed with each of the enzymes used in the present example.

Once all the components were mixed and homogenized, said mixture was incubated at the maximum temperature of activity of each enzyme. The level of hydrolysis was assessed after 1, 12, and 24 hours of incubation and the results were compared against a control that is performed and only differs from the test solutions by the absence of enzyme.

The following table shows the results corresponding to the different tests performed in Example 1.

| ENZYME | Nature | pH | Denaturing agent | Reducing agent | % solubilized | Time (h) |
|---|---|---|---|---|---|---|
| Papain | Cysteine protease endopeptidase | 6.2 | SDS | $Na_2SO_3$ | 0 | 24 |
| Bromelain | Cysteine protease endopeptidase | 6.2 | SDS | $Na_2SO_3$ | 0 | 24 |
| Ficin | Cysteine protease endopeptidase | 6.2 | SDS | $Na_2SO_3$ | 0 | 24 |
| Protease K | Cysteine protease endopeptidase | 7 | SDS | $Na_2SO_3$ | 0 | 24 |
| Pepsin | Endopeptidase | 4 | SDS | $Na_2SO_3$ | 0 | 24 |
| Papain | Cysteine protease endopeptidase | 6.2 | SDS | $Na_2S_2O_4$ | 0 | 24 |
| Bromelain | Cysteine protease endopeptidase | 6.2 | SDS | $Na_2S_2O_4$ | 0 | 24 |
| Ficin | Cysteine protease endopeptidase | 6.2 | SDS | $Na_2S_2O_4$ | 0 | 24 |
| Protease K | Cysteine protease endopeptidase | 7 | SDS | $Na_2S_2O_4$ | 0 | 24 |
| Pepsin | Endopeptidase | 4 | SDS | $Na_2S_2O_4$ | 0 | 24 |

| ENZYME | Nature | pH | Denaturing agent | $HOCH_2SO_2Na$ | % solubilized | Time (h) |
|---|---|---|---|---|---|---|
| Papain | Cysteine protease endopeptidase | 6.2 | SDS | $HOCH_2SO_2Na$ | 100 | 12 |
| Bromelain | Cysteine protease endopeptidase | 6.2 | SDS | $HOCH_2SO_2Na$ | 100 | 12 |
| Ficin | Cysteine protease endopeptidase | 6.2 | SDS | $HOCH_2SO_2Na$ | 0 | 24 |
| Protease K | Cysteine protease endopeptidase | 7 | SDS | $HOCH_2SO_2Na$ | 0 | 24 |
| Pepsin | Endopeptidase | 4 | SDS | $HOCH_2SO_2Na$ | 0 | 24 |

| ENZYME | Nature | pH | Denaturing agent | Reducing agent | % solubilized | Time (h) |
|---|---|---|---|---|---|---|
| Papain | Cysteine protease endopeptidase | 6.2 | SDS | $Na_2S_2O_5$ | 100 | 1 |
| Bromelain | Cysteine protease endopeptidase | 6.2 | SDS | $Na_2S_2O_5$ | 100 | 1 |
| Ficin | Cysteine protease endopeptidase | 6.2 | SDS | $Na_2S_2O_5$ | 50 | 24 |
| Protease K | Cysteine protease endopeptidase | 7 | SDS | $Na_2S_2O_5$ | 80 | 24 |
| Pepsin | Endopeptidase | 4 | SDS | $Na_2S_2O_5$ | 0 | 24 |

| | | | | | |
|---|---|---|---|---|---|
| Papain | Cysteine protease endopeptidase | 6.2 | SDS | DTT | 100 | 1 |
| Bromelain | Cysteine protease endopeptidase | 6.2 | SDS | DTT | 100 | 1 |
| Ficin | Cysteine protease endopeptidase | 6.2 | SDS | DTT | 50 | 24 |
| Protease K | Cysteine protease endopeptidase | 7 | SDS | DTT | 80 | 24 |
| Pepsin | Endopeptidase | 4 | SDS | DTT | 0 | 24 |

Therefore, it can be concluded based on the preceding results that, only three (sodium hydroxymethanesulfinate, sodium metabisulfite, and DTT) of the different tested reducing agents would allow 100% hydrolysis of the tested enzymes under the described conditions, and more specifically sodium metabisulfite and DTT showed better results.

Collagen and GAGs were quantified with the hydrolysates obtained after using DTT and sodium metabisulfite. In the case of the hydrolysates obtained with DTT, interferences preventing proper quantification were observed. Therefore, in embodiments in which accurate quantification of the various components of the eggshell membrane is to be performed, use of sodium metabisulfite as a reducing agent is preferred.

Example 2

The following example sought to verify the optimum concentration of sodium metabisulfite ($Na_2S_2O_5$) that will be used, for which papain was used as an enzyme and different concentrations of $Na_2S_2O_5$ were used. Furthermore, whether or not there is a need to use the denaturing agent, SDS, was assessed, so use of said SDS was omitted when the maximum concentration of $Na_2S_2O_5$ was used, a complete absence of hydrolysis being obtained, as demonstrated in the table below.

Specifically, a solution for solubilizing 10 mg of eggshell membrane/ml of solution was prepared. Said solution only contained 100 mM sodium metabisulfite ($Na_2S_2O_5$) (1). Three other similar solutions were prepared with an increasing order of concentration of $Na_2S_2O_5$, i.e., 5 mM (2), 50 mM (3), and 100 mM (4), but in this case they contained 0.5-5% SDS in 50 mM HEPES buffer adjusted to pH 6.2 with a pH-meter. It was verified that the optimum range of sodium metabisulfite ($Na_2S_2O_5$) for the present invention is between 50 and 150 mM. Papain previously activated in a 0.15 M sodium chloride solution was added such that the final concentration of the enzyme in the mixture was 0.05-0.5%. Once all the components were mixed and homogenized, said mixture was incubated at 38° C. for 12 h. The level of hydrolysis was evaluated after 12 hours of incubation and the results were compared against a control that is performed and only differs from the test solutions by the absence of enzyme. A solution similar to the control was obtained for samples 1 and 2, a completely clear, amber-colored solution demonstrating the complete disappearance of the eggshell membrane to be dissolved was obtained for solution 4, and an intermediate result was obtained for solution 3.

The obtained results are shown in the following table.

| Papain | (1) $Na_2S_2O_5$ 100 mM | (2) SDS + $Na_2S_2O_5$ 5 mM | (3) SDS + $Na_2S_2O_5$ 50 mM | (4) SDS + $Na_2S_2O_5$ 100 mM |
|---|---|---|---|---|
| % solubilized | 0 | 0 | 70 | 100 |

Example 3

In order to optimize the amount of membrane that could be hydrolyzed with a papain concentration of 0.1%, different dilutions of the membrane to be hydrolyzed were prepared, where the best results were obtained for a membrane concentration between 20 and 150 mg/ml (although the invention also works in the range of between 5 and 155 mg/ml), and more specifically 70 mg/ml, as can be seen in the table below.

Specifically, different solutions with different amounts of eggshell membrane were prepared such that final concentrations with respect to the total solution volume of 20, 30, 40, 50, 70, 100, and 150 mg of eggshell membrane/ml of solution were obtained. The solution contained 100 mM sodium metabisulfite ($Na_2S_2O_5$), 0.5-5% SDS in 50 mM HEPES buffer adjusted to pH 6.2 with a pH-meter. 1% papain previously activated in a 0.15 M sodium chloride solution was then added such that the concentration of the enzyme with respect to the final volume of the mixture was 0.05-0.5%. Once all the components were mixed and homogenized, said mixture was incubated at 38° C. for 12 h and the results were compared against a control that is performed and only differs from the test solutions by the absence of enzyme. A clear, amber-colored solution was obtained, the color of which intensifies as the membrane concentration increases, in addition to the presence of a precipitate increasing, which indicates a lower level of hydrolysis.

| Membrane, mg/ml | Papain, % | Time, h | % of hydrolyzation |
|---|---|---|---|
| 20 | 0.1 | 12 | 100 |
| 30 | 0.1 | 12 | 100 |
| 50 | 0.1 | 12 | 100 |
| 70 | 0.1 | 12 | 100 |
| 100 | 0.1 | 12 | 90 |
| 150 | 0.1 | 12 | 80 |

Example 4

Determination of Glycosaminoglycans (GAGs) in an Egg Membrane

GAGs are one of the components that are found in one of the highest proportions in egg membrane. The amount of beneficial effects that GAGs can provide to the human body following their intake has been described on countless occasions; it is therefore of vital importance to provide a technique which allows obtaining reliable and repetitive results. One of the methods most widely used for quantifying the GAG content of organic material and providing some of the best results is the carbazole method described in detail in the Royal Spanish Pharmacopoeia (Real Farmacopea Española), $2^{nd}$ edition, January 2002, 1472. One of the constraints of this method is that the samples to be quantified must be water-soluble. Given the insolubility of egg membrane, the primary requirement was to achieve solubilization of the egg membrane in water.

In order to validate the method and before quantifying the hydrolysates, different concentrations (0.02, 0.04, 0.06, and 0.08 mg/ml) of a known GAG, i.e., hyaluronic acid (HA), were used. The results thus obtained showed that the carbazole method actually allowed reliably quantifying the presence of a GAG such as HA in a solution given that the coefficient of correlation obtained was $r^2=0.9937$).

Once the carbazole technique was validated, in order to be able to measure GAGs in the hydrolyzed egg membrane, GAGs in hydrolysates which were obtained with better results in Example 1 described above, specifically those which were obtained using sodium metabisulfite (A) and DTT (B) as a reducing agent, were quantified.

The same was performed with both hydrolysates as described below.

The following reagents were first prepared: a solution of 0.95 g of sodium tetraborate in 100 ml of concentrated sulfuric acid, a solution of 0.125 g of carbazole in 100 ml of anhydrous ethanol, and finally a stock solution of D-glucuronic acid in 100 ml of water.

Once the required reagents as described above were prepared, 100 µl of each of hydrolysates A and B were diluted in 1000 µl of water. The test tubes were placed in an ice bath and 1.0 ml of test dilutions A and B was added. 5 ml of the previously prepared sodium tetraborate solution kept in the ice bath were added to each tube. Once the test tubes were hermetically closed with glass stoppers, the content was stirred, and the tubes were placed in a thermostatted bath at 90° C. for 10 minutes. The tubes were then cooled in an ice bath and 200 µl of a previously prepared alcoholic solution of carbazole were finally added to each tube. The tubes were again placed in the bath at 90° C. for 15 minutes after they were stoppered again and stirred, and the absorbance of test solutions A and B at 530 nm was measured after cooling at room temperature. Along with the test samples, the same method was performed with 4 samples with D-glucuronic acid concentrations of 6.5, 20, 40, and 65 µg/ml obtained from the stock dilution to enable plotting a standard straight line.

The standard samples and samples obtained from test sample A showed a pink color similar to the color previously obtained when performing the technique validation test using HA.

However, test sample B showed a brown color in which it was impossible to obtain absorbance results. Given that the only difference of both test samples A and B was the presence of a different reducing agent, it was concluded that DTT caused interferences with the reagents of the carbazole technique, and it was therefore concluded that the only reducing agent which can be used for hydrolyzing the membrane for subsequent GAG quantification was sodium metabisulfite.

The technique thus used provided a GAG result of 5.08±0.4784 µg of glucuronic acid/mg of Ovomet (egg membrane obtained by Eggnovo S.L.).

Example 5

Determination of Collagen in an Egg Membrane

Collagen is one of the major components of eggshell membrane. The levels of collagen in egg membrane are determined in many published papers; however, the different results show fluctuations which to a certain extent are due to the different quantification techniques used. This is due to the fact that all these techniques require prior membrane solubilization for subsequent analysis; therefore the level of hydrolyzation of the membrane for solubilization is a vital parameter so that the collagen values that are obtained are representative of reality. There are now colorimetric quantification methods, such as the Sircol® method which, despite having the advantage of being carried out rapidly, always has a lower precision compared to the precision of a method based on HPLC determinations.

The proposed collagen quantification method is based on the hydroxyproline (Hyp) quantification method according to Hutson et al. 2003 (J. Chromatogr. B 791: 427-430), with some modifications. The results obtained previously by Yu-Hong Zhao and Yu-Jiechi (Biotechnology 8 (2):254-258 (2009), Characterization of Collagen from Eggshell Membrane), demonstrating that the collagen of egg membrane is a type I collagen, a decision is made to use type I collagen as a standard for the determination. Furthermore, according to Dziewiatkowski D. et al, 1972. ("Epimerization of trans-4-hydroxy-L-proline to cis-4-hydroxy-D-proline during acid hydrolysis of collagen") it is known that two hydroxyproline isomers, i.e., L- and D-Hyp, are obtained during collagen degradation.

Based on the foregoing and before validating the method, L-Hyp, D-Hyp, and proline standards from Sigma-Aldrich were injected in the HPLC, these standards being prepared in a matrix at different concentrations to enable identifying peaks corresponding to each of the isomers and proline expected to be obtained.

Once the characteristic peaks of the two hydroxyproline isomers and of proline were determined and before quantifying the hydrolysates, a series of solutions were prepared with different concentrations of mouse tail type I collagen acquired from Sigma-Aldrich, collagen degradation chromatographic profile being obtained.

Given that the combination of the hydrolysis solution consisting of SDS, sodium metabisulfite, and papain was the one that had shown better results with the tests conducted up until now, a solution thus constituted and with a concentration of the membrane to be dissolved of 10 mg/ml was used.

100 µl of the hydrolysate thus obtained were then taken and 500 µl of 6 N HCl were added, 400 µl were taken after homogenization, and another 3600 µl of 6 N HCl were added. 100 µl of 2 mM sarcosine were added thereto and it was kept in an oven at 110° C. for 18 hours in tubes that are closed with their cover. Once cooled, it was neutralized with 6 N NaOH, bringing it to a pH of 9.5. 900 µl were taken from this solution and 200 µl of 0.7 M borate buffer, pH 9.5, 100 µl of o-phthalaldehyde (OPA) solution, 100 µl of iodoacetamide reagent, and 300 µl of 9-fluorenylmethyl chloroformate reagent (Fmoc-HCl) were added thereto, stirring with vortex for 10 seconds and leaving to stand for 1 minute after adding each of the solutions. Finally, it was washed three times with 2 ml of diethyl ether, stirring for 30 seconds in each case, two clearly differentiated phases being obtained in each tube, an upper phase which is the organic phase and a lower phase which is the aqueous phase. The organic phase was discarded, and part of the aqueous phase was taken and injected in the HPLC.

The chromatographic conditions were as follows: 5 µm Xterra® C18 column having the dimensions of 25×0.46 mm. The phases used were A: 3% acetate buffer, pH 4.3, and B: acetonitrile; in an isocratic ratio of 65/35, respectively, at a flow rate of 1 ml/min, and with a column temperature of 25° C.

The chromatograms were optimized after 20 minutes using a fluorescence detector at an excitation wavelength of 265 nm and without an emission filter.

The results thus obtained showed 35.31±4.8% of collagen present in Ovomet (egg membrane obtained by Eggnovo S.L.).

For example, the following results are known in the prior art:

U.S. Pat. No. 6,176,376 B1-10% collagen

Yu-hong Zhao et al. 2009. Characterization of collagen from eggshell membrane. *Biotechnology*, 8: 254-258- 10% collagen.

The present invention shows better results than those observed in the literature for egg membrane, which demonstrates that, taking into account that all the results are obtained from membrane hydrolysates, the hydrolyzation of the membrane obtained by the method proposed in this patent is superior to that described in other publications.

Example 6

In Vitro Studies of Cell Viability and Hydrolysate Absorption

Once the main biological components present in Ovomet were quantified, an in vitro study was designed to enable confirming, on one hand, the non-toxicity of the hydrolysates obtained from the technique described herein, and on the other hand, the absorption rate of said hydrolysates in human beings.

To enable conducting both studies, a Caco-2 cell model forming a monolayer after a maturation process was used. To that end, the study was conducted as described in detail below:

Cells were seeded at a density of $3\times10^3$ per insert of 24 $mm^2$ and area of 4.67 $cm^2$ in porous polyester (PET) membrane filters (0.4 µm) having 6 wells (Transwell 3450; Costar, Corning). These inserts have two separated compartments, an apical compartment and another basal compartment. The cells were seeded in each apical compartment dissolved in a volume of 1.5 ml of culture medium. 2.5 ml of culture medium were then added to the basal compartment.

For the cells to grow in the inserts, fresh culture medium was added thereto every two days until 21 days lapsed so that cell growth was suitable for the purpose of achieving the proper formation and maturation of the multiple cell layers.

Once 21-day period following cell seeding ended, the cell monolayers were checked in order to determine if they had intercellular gaps allowing the passage of any substance between the apical part and the basal part, in order to assure that the passage of a substance to be tested only occurred exclusively through the cells and not through any gap that may exist between them. To that end, transepithelial resistance (TER) was measured using a Millicell ohmmeter (ERS model, Millipore Corp., Billerica Mass.; USA). Only those cell monolayers with resistance data between 500 and 800 $\Omega \cdot cm^2$ were taken as suitable.

Once the 21-day period ended and the state of the cell monolayers was confirmed to be correct, the culture medium was removed and the cells were bathed in a physiological solution referred to as HBSS (Hank's balanced salt solution) supplemented with 25 mM HEPES, pH 7.4 (Kis O et al., Pharm Res (2013) 30:1050-1064). The hydrolysate to be tested was produced as described below: 50 mg/ml of OVOMET dissolved in 50 mM HEPES, 1% SDS, and 100 mM sodium metabisulfite, and 0.1% bromelain for 12 hours, under the conditions described above in Example 1.

Cell Viability Analysis by Means of Trypan Blue

Once the hydrolysate was obtained, different serial dilutions of the hydrolysate in HBSS (1:200, 1:400, 1:600, 1:800, 1:1000), which were incubated with the cell culture at 37° C. and at 5% $CO_2$ for 4 hours, were made. After this time period elapsed, the culture medium was removed, and 400 µl of trypsin subsequently neutralized with 600 µl of PBS and 2.5% fetal bovine serum were added. After successive washing, the cells were transferred to Eppendorf tubes which were centrifuged at 5000 rpm for 5 minutes. The supernatant was removed and the precipitate was resuspended in 300 µl of PBS and fetal bovine serum at the same concentrations as in the case described above.

To analyze cell viability, 50 µl of sample were taken and mixed with 50 µl of 4% trypan blue. The samples were loaded in a Bürker chamber, observed under a light microscope, and the cells of 20 fields per sample were counted, distinguishing living cells from dead cells.

The following selection criteria were established to select the optimum dilutions that showed better cell viability rates:

a—The cells do not detach once they are contacted with the dilutions.

b—The count of dead cells in the Bürker chamber does not exceed 10%.

c—The cells observed under microscope have a suitable shape (rounded with smooth edges).

It was observed that viability was greater than 90% in 1:400, 1:600, 1:800, and 1:1000 dilutions, with 1:400, 1:600, and 1:800 dilutions being chosen for the study.

Transport and Absorption Study

Once Caco-2 cell monolayers, the proper preparation of which had been tested as described above, were available, the cells were pre-incubated. To that end, a transport solution was added to both sides (both the apical side and the basal side) of the cell culture for 1 hour at 37° C. and 5% $CO_2$. Once pre-incubation ended, the transport solution was removed and the solution containing the membrane hydrolysate at different dilutions (1:400, 1:600, and 1:800) was added to the apical compartment for incubation at 37° C. and with 5% $CO_2$, for 90, 120, 150, and 180 minutes. At the last point, a sample was further taken from the apical compartment. Hydroxyproline (Hyp) concentration was determined by means of HPLC on the basal side as an indicator of the intestinal transport of Ovomet hydrolysate.

The following table shows the results of the transport study. Said table has the ratio corresponding to the chromatographic areas of Hyp obtained in the different dilutions and at different times. The underlined values are Hyp values corresponding to the transport solution with different dilutions of Ovomet hydrolysate.

| Time, min. | |
|---|---|
| Solution OVOMET, 1/400 | 0.33406326 |
| 90 | 0.02141620 |
| 120 | 0.1265950 |
| 150 | 0.04080866 |
| 180 | 0.03207032 |
| OVOMET Solution, 1/600 | 0.33406326 |
| 90 | NQ |
| 120 | 0.03725867 |
| 150 | 0.02343651 |
| 180 | 0.01011769 |
| Solution OVOMET, 1/800 | 0.20823490 |
| 90 | 0.02665078 |
| 120 | 0.01648812 |
| 150 | 0.01379862 |
| 180 | 0.00788849 |

With these results, the cumulative percentage was calculated considering the values relative to the different hydrolysate concentrations.

| | Dilution of Ovomet hydrolysate | | |
|---|---|---|---|
| | 1/400 | 1/600 | 1/800 |
| | Cumulative % of hydrolyzed Ovomet solution | | |
| Time | 100% | 65.40% | 50% |
| 90 | 6.41 | NQ | 6.39 |
| 120 | 10.20 | 11.52 | 10.35 |
| 150 | 22.41 | 18.77 | 13.67 |
| 180 | 32.01 | 21.90 | 15.56 |

With these values, linear regressions were plotted based on the cumulative percentage of OVOMET solution, where lines with an increasingly greater slope are observed the higher the concentration of the tested hydrolysate solution is (see FIG. 1).

Once this data was known, the parameter referred to as "coefficient of apparent permeability" ($P_{app}$) must be known given that there are several models linking the logarithm of $P_{app}$ with absorption in human beings. The following equation was used to calculate $P_{app}$: $P_{app} = Q/A \times Ci$, where Q is the slope of the regression lines previously calculated (cumulative amount over time), A is the Transwell well section, and Ci is the concentration on the apical side. The data thus calculated is shown in the following table.

| Dilution | $P_{app}$ (CM/S) | Log $P_{app}$ |
|---|---|---|
| 1/400 | $1.606\ E^{-05}$ | −4.79 |
| 1/600 | $1.604\ E^{-05}$ | −4.79 |
| 1/800 | $7.495\ E^{-06}$ | −5.12 |

Figure 2:
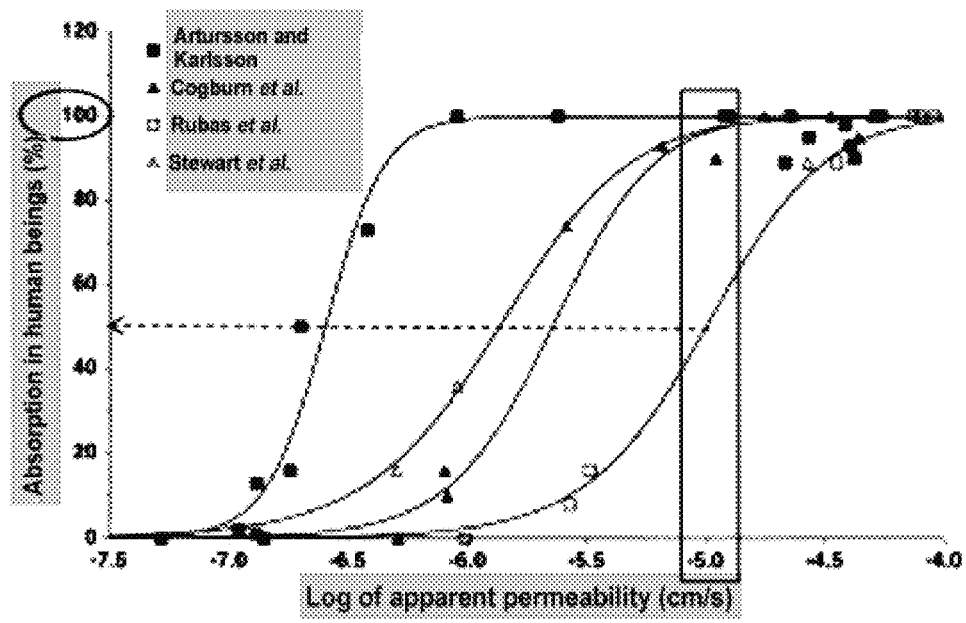
FIG. 2 is a graph showing the % of absorption in human beings as a function of logarithm of apparent permeability.

After knowing the Log $P_{app}$ values as described above, they can be correlated with the fraction absorbed in human beings after oral administration expressed as a % of the dose of the administered product obtained in 4 different laboratories, see FIG. 2.

The following absorption results were obtained depending on the different models mentioned.

| Model | % of absorption |
|---|---|
| Artursson et al. | 100 |
| Cogburn et al. | 95-100 |
| Rubas et al. | 93-100 |
| Stewart et al. | 45-65 |

The mentioned models are disclosed in the following sources:

Artursson et al. 1991. Correlation between oral drug absorption in humans and apparent drug permeability coefficients in human intestinal epithelial (caco-2) cells. *Biochemical and Biophysical Research Communications* 175 (3): 880-5.

Coburn et al. (1991). A model of human small intestinal absorptive cells. A. Transport barrier. Pharmaceutical Research 8 (2): 210-6.

Rubas et al. (1996). Flux measurements across Caco-2 monolayers may predict transport in human large intestinal tissue. Journal of Pharmaceutical Science 85 (2):165-9.

Stewart et al. (1995). Comparison of intestinal permeabilities determined in multiple in vitro and in situ models: relationship to absorption in humans. Pharmaceutical Research 12(5):693-9.

Although the present invention has been described above in reference to specific preferred embodiments, one skilled in the art will understand that various modifications and variations can be applied without departing from the scope of protection defined by the attached claims. Specifically, depending on specific application limits (costs, yield sought, etc.) as well as the purposes of the application (obtaining components that are useful in industry, quantifying components constituting the membrane, etc.), different reducing agents, denaturing agents, buffers, and enzymes, as well as different amounts thereof, may be used.

The invention claimed is:

1. A method for hydrolyzing eggshell membrane, comprising the step of treating eggshell membrane in a solution having a pH in the range between 6 and 7, and comprising a denaturing agent, a reducing agent, a buffer, and an enzyme, wherein the denaturing agent is sodium lauryl sulfate (SDS), the reducing agent is selected from the group consisting of sodium hydroxymethanesulfinate, sodium metabisulfite, and dithiothreitol (DTT), and the enzyme is an endopeptidase selected from the group of cysteine proteases.

2. The method according to claim 1, wherein the reducing agent is selected from the group consisting of sodium metabisulfite and DTT.

3. The method according to claim 2, wherein the reducing agent is sodium metabisulfite.

4. The method according to claim 1, wherein the cysteine endopeptidase is selected from the group consisting of papain and bromelain.

5. The method according to claim 1, comprising the step of treating the eggshell membrane in an amount ranging between 5 and 155 mg/ml, in a solution containing sodium metabisulfite in a range of between 50 and 150 mM, 0.5-5% SDS in 25-50 mM 4-(2-hydroxyethyl)-1-piperazineethanesulfonic acid (HEPES) buffer, adjusted to a pH of 6.2, and a 1% papain solution in sodium chloride in a range of 0.05 to 0.5 M, being added to said solution until the final papain concentration in the solution is 0.05-0.5%.

* * * * *